US010076555B2

(12) United States Patent
Kleinig et al.

(10) Patent No.: US 10,076,555 B2
(45) Date of Patent: *Sep. 18, 2018

(54) METHODS OF INDUCING MELANOGENESIS IN A SUBJECT

(71) Applicant: Clinuvel Pharmaceuticals Limited, Melbourne, Victoria (AU)

(72) Inventors: Michael John Kleinig, Brunswick (AU); Thomas R. Tice, Indian Springs, AL (US); Jay K. Staas, Marylene, AL (US)

(73) Assignee: Clinuvel Pharmaceuticals Limited, Melbourne (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/135,241

(22) Filed: Apr. 21, 2016

(65) Prior Publication Data

US 2016/0235819 A1 Aug. 18, 2016

Related U.S. Application Data

(62) Division of application No. 11/659,178, filed as application No. PCT/AU2005/000181 on Feb. 11, 2005, now Pat. No. 9,345,911.

(60) Provisional application No. 60/599,143, filed on Aug. 4, 2004.

(51) Int. Cl.
| | |
|---|---|
| *A61Q 19/04* | (2006.01) |
| *A61K 38/34* | (2006.01) |
| *A61K 8/64* | (2006.01) |
| *A61K 9/00* | (2006.01) |

(52) U.S. Cl.
CPC .............. *A61K 38/34* (2013.01); *A61K 8/64* (2013.01); *A61K 9/0019* (2013.01); *A61Q 19/04* (2013.01)

(58) Field of Classification Search
CPC .............................. A61K 38/34; A61K 9/0019
See application file for complete search history.

(56) References Cited

U.S. PATENT DOCUMENTS

| | | | |
|---|---|---|---|
| 4,675,189 A | 6/1987 | Kent et al. | |
| 5,049,547 A | 9/1991 | Hruby et al. | |
| 6,165,508 A | 12/2000 | Tracy et al. | |
| 6,495,155 B1 | 12/2002 | Tice et al. | |
| 9,345,911 B2* | 5/2016 | Kleinig ................ | A61K 8/64 |

OTHER PUBLICATIONS

Ugwu et al (1997), Biopharmaceutics & Drug Disposition, vol. 18, 3, 259-269.*
Bhardwaj and Blanchard, "In vitro evaluation of Poly(D,L-lactide-co-glycolide) polymer-based implants containing the α-melanocyte stimulating hormone analog, Melanotan-I", Journal of Controlled Release, 1997; 49-55.
Bhardwaj, "Formulation of PLGA Implant for Controlled Release of Melanotan-1 : Influence of Drug Loading and Composition of Polymer", 1995; 12(9 Suppl): S226, Abstract #PDD 7133.
Bhardwaj, R. and Blanchard J., "Controlled-Release Delivery System for the α-MSH Analog Melanotan-I Using Poloxamer 407", Journal of Pharmaceutical Sciences, vol. 85, No. 9, Sep. 1996, pp. 915-919.
Bhardwaj, R. and Blanchard J., "In vitro characterization and in vivo release profile of a poly (D,L-lactide-co-glycolide)-based implant delivery system for the α-MSH analog, melanotan-I", International Journal of Pharmaceutics, vol. 170, 1998, pp. 109-117.
Bhardwaj, R., et al., "Pharmacologic Response of a Controlled-Release PLGA Formulation for the Alpha-Melanocyte Stimulating Hormone Analog Melanotan-I", Pharmaceutical Research, vol. 17, No. 5, 2000, pp. 593-599.
Bolognia et al., "Hairless Pigmented Guinea Pigs: A New Model for the Study of Mammalian Pigmentation", Pigment Cell Res. Sep. 1990;3(3):150-6.
Box, N. F., et al., "Melanocortin-1 Receptor Genotype is a Risk Factor for Basal and Squamous Cell Carcinoma", The Journal of Investigative Dermatology, vol. 116, No. 2, Feb. 2001, pp. 224-229.
Ceriani, G., et al., "The Neuropeptide Alpha-Melanocyte-Stimulating Hormone Inhibits Experimental Arthritis in Rats", Neuroimmunomodulation, vol. 1, 1994, pp. 28-32.
Chiao, H., et al., "α-Melanocyte-stimulating Hormorne Reduces Endotoxin-induced Liver Inflammation", Journal of Clinical Investigation, vol. 97, No. 9, May 1996, pp. 2038-2044.
Dawson, B. V., et al. "Administration of melanotropic peptides during gestation in the rodent" Toxicology, vol. 77, 1993, pp. 91-101.
De L. Castrucci, A. M., et al. "Enzymological Studies of Melanotropins", Comp. Biochem Physiol., vol. 78B, No. 3, 1984, pp. 519-524.
Dorr, R. T., et al. "Increased Eumelanin Expression and Tanning is Induced by a Superpotent Melanotropin [Nle4-D-Phe7]-α-MSH in Humans", Photochemistry and Photobiology, vol. 72, No. 4, 2000, pp. 526-532.
Dorr, R. T., et al. "Toxicologic studies of a superpotent α-melanotropin, [Nle4, D-Phe7] α-MSH", Investigational New Drugs, vol. 6, 1988, pp. 251-258.
Dorr, R. T., et al. "Toxicology Report—Results of a 30 Day Study of Melanotan IR Given Subcutaneously to Adult Rats." Dept. of Anatomy, School of Medicine, University of Auckland, 1988, pp. 1-23.
Dorr, R.T. "Thirty Day Toxicology Study of Melanotan-I (Nle4-D-Phe7) α-MSH1-13 in Miniature Yucatan Swine", Univ. of Arizona Cancer Center and Dermatology Dept., Arizona Health Sciences Center, Jun. 1993, pp. 1-45.
Dwyer, T., et al., "The Use of Spectrophotometry to Estimate Melanin Density in Caucasians", Cancer Epidemiology, Biomarkers & Prevention, vol. 7, Mar. 1998, pp. 203-206.
Fitzpatrick, T. B., "The Validity and Practicality of Sun-Reactive Skin Types I Through VI", Arch Dermatol, vol. 124, Jun. 1988, pp. 869-871.

(Continued)

*Primary Examiner* — Prema Maria Mertz
(74) *Attorney, Agent, or Firm* — Birch, Stewart, Kolasch & Birch, LLP

(57) ABSTRACT

Described herein are methods and compositions for inducing melanogenesis in a human subject. The method comprises administering to a subject an alpha-MSH analogue, in an effective amount and time to induce melanogenesis by the melanocytes in epidermal tissue of subject without inducing homologous desensitization of the melanocortin-1 receptors.

22 Claims, 7 Drawing Sheets

(56) References Cited

OTHER PUBLICATIONS

Hadley, M. E., et al., "[NLE4, D-PHE7]-α-MSH: A Superpotent Melanotropin That "Irreversibly" Activates Melanoma Tyrosinase", Endocrine Research, vol. 11, (3-4), 1985, pp. 157-170.

Levine et al., "Stimulation of Follicular Melanogenesis in the Mouse by Topical and Injected Melanotropins", Journal of Investigative Dermatology, 1987; 89: 269-273.

Levine, N., et al., "Effects of a potent synthetic melanotropin, Nle4-D-Phe7-α-MSH (Melanotan-I) on tanning: a dose-ranging study", Journal of Dermatological Treatment, vol. 10, 1999, pp. 127-132.

Levine, N., et al., "Induction of Skin Tanning by Subcutaneous Administration of a Potent Synthetic Melanotropin", JAMA, vol. 266, No. 19, Nov. 1991, pp. 2730-2732 & 2734-2736.

Lima and Rodrigues Junior,: "Poly-D Llactide-co-glycolide microspheres as a controlled release antigen delivery system", Brazilian Journal of Medical and Biological Research, 1999; 32: 171-180.

Lipton, J. M., et al., "Antiinflammatory Effects of the Neuropeptide α-MSH in Acute, Chronic, and Systemic Inflammation", Annals New York Academy of Sciences, Nov. 1994, vol. 741, pp. 137-148.

Palmer, J. S., et al., "Melanocortin-1 Receptor Polymorphisms and Risk of Melanoma: Is the Association Explained Solely by Pigmentation Phenotype?", American Journal of Human Genetics, vol. 66, 2000, pp. 176-186.

Sanchez-Mas, J., et al., "Role of G Protein-Coupled Receptor Kinases in the Homologous Desensitization of the Human and Mouse Melanocortin 1 Receptors", Molecular Endocrinology, vol. 19, No. 4, Apr. 2005, pp. 1035-1048.

Sawyer, T. K., et al., "4-Norleucine, 7-D-phenylalanine-α-melanocyte-stimulating hormone: A highly potent α-melanotropin with ultralong biological activity", Proc. Nat'l. Academy Sci., vol. 77, No. 10, Oct. 1980, pp. 5754-5758.

Thody, A. J., et al., "Pheomelanin as well as Eumelanin Is Present in Human Epidermis", The Journal of Investigative Dermatology Inc., vol. 97, No. 2, 1991, pp. 340-344.

Ugwu et al., "Skin Pigmentation and Pharmacokinetics of Melanotan-I In Humans", Biopharmaceutics & Drug Disposition, 1997; 18: 259-269.

Valverde, P., et al., "Variants of the melanocyte-stimulating hormone receptor gene are associated with red hair and fair skin in humans" Nature Genetics, vol. 11, 1995, pp. 328-330.

Website downloaded from: yourtotalhealth.ivillage.com/sun-exposure-can-damage-darker-skin-too.print.html; Nov. 19, 2009; 3 pages total.

Andersen et al., "The Guinea-Pig: an Animal Model for Human Skin Absorption of Hydrocortisone, Testosterone and Benzoic Acid?" British Journal of Dermatology, vol. 102, 1980, pp. 447-453.

Barbero et al., "Pig and Guinea Pig Skin as Surrogates for Human In Vitro Penetration Studies: A Quantitative Review," Toxicology in Vitro, vol. 23, 2009 (published online Oct. 26, 2008), pp. 1-13.

Bhardwaj, "Formulation of Controlled-Release Delivery Systems for the Alpha-Melanocyte Stimulating Hormone Analog, Melanotan-I," Dissertation (published by UMI), 1997, pp. 1-146 (148 pages total).

Cone et al., "The Melanocortin Receptors: Agonists, Antagonists, and the Hormonal Control of Pigmentation," Recent Progress in Hormone Research, vol. 51, 1996, pp. 287-318 (33 pages total).

De Luca et al., "Human Epithelial Cells Induce Human Melanocyte Growth In Vitro but Only Skin Keratinocytes Regulate its Proper Differentiation in the Absence of Dermis," Journal of Cell Biology, vol. 107, Nov. 1988, pp. 1919-1926.

Guest, "Rats: Test Results That Don't Apply to Humans," Personal Care Truth or Scare, retrieved from URL:http://license.icopyright.net/3.12537?icx_id=3750, Apr. 14, 2011, pp. 1-3.

Ha et al., "Animal Models of Melanoma," JID Symposium Proceedings, Nov. 2005, pp. 86-88.

Hoath et al., "The Organization of Human Epidermis: Functional Epidermal Units and Phi Proportionality," The Journal of Investigative Dermatology, vol. 121, No. 6, Dec. 2003, pp. 1440-1446.

Hönigsmann et al., "Immediate Pigment Darkening Phenomenon. A Reevaluation of Its Mechanisms," J Invest Dermatol, vol. 87, No. 5, Nov. 1986 (presented in part at the 13th Annual Meeting of the American Society for Photobiology, Jun. 23-27, 1985), pp. 648-652 (6 pages total).

Krieger et al., "ACTH, β-Lipotropin, and Related Peptides in Brain, Pituitary, and Blood," Recent Progress in Hormone Research, vol. 36, 1980, pp. 277-344.

Liu et at, "Light Microscopic, Electron Microscopic, and Immunohistochemical Comparison of Bama Minipig (Sus scrota domestica) and Human Skin," Comparative Medicine, vol. 60, No. 2, Apr. 2010, pp. 142-148.

Miyamura et al., "Regulation of Human Skin Pigmentation and Responses to Ultraviolet Radiation," Pigment Cell Res., vol. 20, 2006, pp. 2-13.

Moan et al., "Immediate Pigment Darkening: its Evolutionary Roles May Include Protection Against Folate Photosensitization," The FASEB Journal, vol. 26, Mar. 2012, pp. 971-975.

Routaboui et al., "Immediate Pigment Darkening: Description, Kinetic and Biological Function," Eur J Dermatol, vol. 9, No. 2, Mar. 1999, pp. 95-99 (abstract only provided).

Santiago-Walker et al., "Melanocytes: From Morphology to Application," Skin Pharmacol Physiol, vol. 22, 2009 (published online Feb. 4, 2009), pp. 114-121.

Smalley, "A Pivotal Role for ERK in the Oncogenic Behaviour of Malignant Melanoma?" Int. J. Cancer, vol. 104, 2003, pp. 527-532.

Varki et al., "Comparing the Human and Chimpanzee Genomes: Searching for Needles in a Haystack," Genome Res., vol. 15, 2005, pp. 1746-1758 (15 pages total).

Young, "Acute Effects of UVR on Human Eyes and Skin," Progress in Biophysics and Molecular Biology, vol. 92, 2006 (published online Feb. 28, 2006), pp. 80-85.

* cited by examiner of induction

METHODS OF INDUCING MELANOGENESIS IN A SUBJECT

CROSS-REFERENCE TO RELATED APPLICATIONS

This application is a Divisional of copending application Ser. No. 11/659,178 filed on Jul. 15, 2008, which is the U.S. National Phase of PCT/AU2005/000181, filed Feb. 11, 2005, and which claims priority to U.S. Provisional Application No. 60/599,143 filed on Aug. 4, 2004. The entire contents of all of the above applications is hereby incorporated by reference.

BACKGROUND

The melanocortins include a family of peptide hormones that induce pigmentation by interaction with melanocortin-1 receptors (MC1R) in the epidermis.[1] The primary pigmentary hormone that is released from the pars intermedia of the pituitary gland in some non-human animals, and from UV exposed keratinocytes in human skin, is alpha melanocyte stimulating hormone (alpha-MSH).[1] This 13 amino acid peptide binds to MC1R to induce cyclic AMP-mediated signal transduction, which leads to the synthesis of melanin polymers from DOPA precursors.[1] Two types of melanins can be expressed in humans. The brownish-black pigment eumelanin is believed to convey protection from sun damage, whereas the reddish, sulfur-containing pigment, pheomelanin, is often expressed in light-skinned human populations that report a poor tanning response to sunlight.[2] These poorly-tanning, easily-burning populations often possess defects in the MC1R gene.[3] and are generally thought to be at a greater risk of developing both melanoma and non-melanoma skin cancers.[4,5]

It has previously been disclosed that a super-potent derivative of alpha-MSH, Melanotan (Nle$^4$-D-Phe$^7$-alpha MSH, also referred to herein as "Melanotan-1" or "MT1"), can induce tanning in human volunteers.[6] Melanotan contains two amino acid substitutions and is approximately 100 to 1,000-fold more potent than the native hormone at inducing pigmentation in experimental systems such as the frog skin bioassay or in cultured human keratinocytes.[7] In humans, Melanotan primarily induces eumelanin synthesis in the skin in concert with its tanning effect.[8] Although melanotropins have been postulated to affect immunologic changes,[9,10,11] all of the prior trials reported only minimal side effects such as facial flushing and transient GI upset, unless doses greater than those needed for tanning were administered.[12]

There is compelling evidence that melanotropic peptides may provide a potential for increasing melanin pigmentation of human skin. Synthetic MSH may be used to enhance skin pigmentation of normal or light-skinned individuals to protect them from the hazards of solar radiation. Several studies have suggested that individuals whose skin tends to burn easily on exposure to the sun and does not tan readily are at higher risk of both nonmelanoma skin tumors and of cutaneous melanoma.[16,17,18] There is unambiguous evidence that UV radiation is responsible for skin cancer in humans. In the face of increased deterioration of the ozone layer and the increasing incidence of and mortality from skin cancer, the ability to stimulate the skin's own "protective mechanism" of tanning may prove extremely important as photo-protective strategy.

Accordingly, described herein are methods for inducing melanogenesis in a human subject by administering alpha-MSH analogues to the subject at greatly reduced plasma levels, which surprisingly leads to increased melanin density levels in the subject. By increasing melanin levels in a subject, it is possible to reduce or prevent the occurrence of UV radiation-induced skin damage in the subject. Additionally, the reduced amount of alpha-MSH analogue that is required in the methods described herein avoids undesirable side effects associated with higher doses.

SUMMARY

Described herein are methods for inducing melanogenesis in a subject. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. Like numbers represent the same elements throughout the figures.

DETAILED DESCRIPTION

Figure 1:
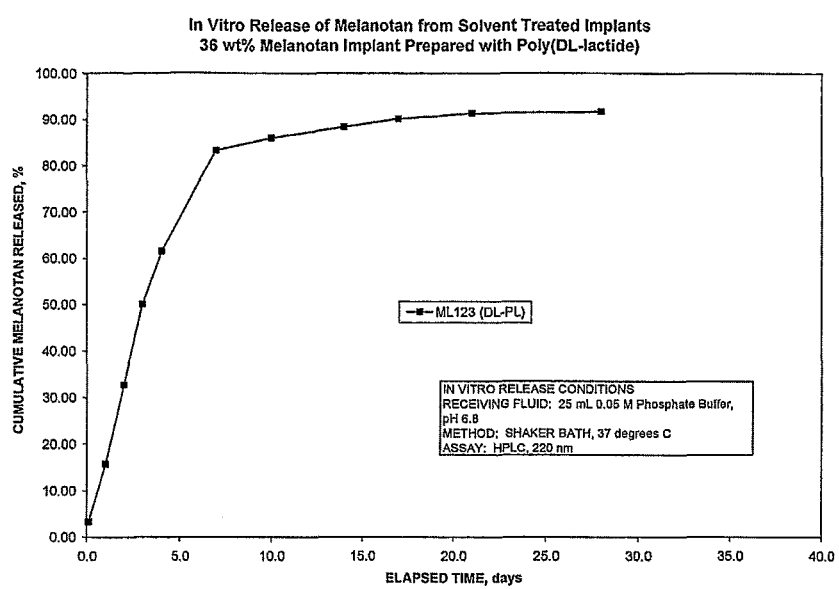
FIG. 1 shows the in vitro release of Melanotan from implants treated with ethyl acetate.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

By "contacting" is meant an instance of exposure by close physical contact of at least one substance to another substance. For example, contacting can include contacting a substance, such as a pharmacologic agent, with a cell. A cell can be contacted with a test compound, for example, an alpha-MSH analogue, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the test compound is present at physiologically effective levels or at presumed physiologically effective levels in the medium or extracellular fluid bathing the cell.

By "prevent" or "preventing" means the administration of a composition to a subject or a system at risk for an undesirable condition. The condition can include a disease or a predisposition to a disease. Prevention can range from a reduction in the severity of the condition to the complete ablation of the condition.

By "effective amount and time" means a therapeutic amount and time needed to achieve the desired result or results, e.g., inducing melanogenesis in a subject.

By "induce" means initiating a desired response or result that was not present prior to the induction step. The term "induce" also includes the term "potentiate."

The term "potentiate" means sustaining a desired response at the same level prior to the potentiating step or increasing the desired response over a period of time.

The term "melanogenesis" as referred to herein is defined as the ability of a subject to produce melanins by melanin-producing cells, or melanocytes.

The term "homologous desensitization" as referred to herein is defined as the inhibition of a cellular response upon continuous exposure to an agonist.

The term "epidermal tissue" as referred to herein includes in particular the skin of a subject.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different alpha-MSH analogues and biodegradable polymers are disclosed and discussed, each and every combination and permutation of the alpha-MSH analogue and biodegradable polymer are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Described herein are methods for inducing melanogenesis in a human subject. The methods herein increase melanin production without inducing homologous desensitization of the melanocortin-1-receptors of the subject. This is accomplished by administering alpha-MSH analogues to the subject so that low concentrations of the alpha-MSH analogue are present in the plasma of the subject. In general, higher doses of alpha-MSH analogue are required to increase melanin production in a subject. However, undesirable side effects can occur when high doses of alpha-MSH analogue are administered. By increasing melanin production in a subject, it is possible to prevent the occurrence of UV radiation-induced skin damage in a subject that would normally be susceptible to such damage.

In one aspect, the method for inducing melanogenesis in a human subject comprises administering to the subject an alpha-MSH analogue in an effective amount and time to induce melanogenesis by the melanocytes in epidermal tissue of the subject without inducing homologous desensitization of the melanocortin-1 receptors of the subject.

In another aspect, described herein are methods for inducing melanogenesis in a human subject, comprising administering to the subject an effective amount of an alpha-MSH analogue to induce melanogenesis by the melanocytes in epidermal tissue of the subject, wherein the alpha-MSH analogue is administered at a level not exceeding 10 ng/ml in the plasma of the subject for a period of at least 24 hours.

In yet another aspect, the invention provides a composition for inducing melanogenesis in a human subject, wherein the composition administers an alpha-MSH analogue to the subject in an effective amount and time to induce melanogenesis by the melanocytes in epidermal tissue of the subject without inducing homologous densitization of the melanocortin-1 receptors of the subject.

In this aspect, the invention also provides a composition for inducing melanogenesis in a human subject, wherein the composition administers an alpha-MSH analogue to the subject at a level not exceeding 10 ng/ml in the plasma of the subject for a period of at least 24 hours.

The term "alpha-MSH analogue" referred to herein is defined as a derivative of alpha-MSH which exhibits agonist activity for the melanocortin-1 receptor (MC1R), the receptor to which alpha-MSH binds to initiate the production of melanin within a melanocyte. Such derivatives include derivatives in which (i) one or more amino acid residues are deleted from the native alpha-MSH molecule at the N-terminal end, the C-terminal end, or both; and/or (ii) one or more amino acid residues of the native alpha-MSH molecule are replaced by another natural, non-natural or synthetic amino acid residue; and/or (iii) an intramolecular interaction forms as a cyclic derivative.

The use of any alpha-MSH analogue is contemplated in the methods described herein. Several derivatives of α-MSH have been synthesized.[19] In one aspect, the alpha-MSH analogues described in U.S. Pat. Nos. 4,457,864, 4,485,039, 4,866,038, 4,918,055, 5,049,547, 5,674,839 and 5,714,576 and Australian Patents Nos. 597630 and 618733, which are herein incorporated by reference for their teachings with respect to alpha-MSH analogues and their synthesis thereof, can be used herein.

In one aspect, the alpha-MSH analogue may be a compound as disclosed in Australian Patent No. 597630, selected from:
(a) compounds of the formula:

Ac-Ser-Tyr-Ser-M-Gln-His-D-Phe-Arg-Trp-Gly-Lys-Pro-Val-NH$_2$ wherein M is Met, Nle or Lys; and
(b) compounds of the formula:

R$_1$-W-X-Y-Z-R$_2$ wherein
R$_1$ is Ac-Gly-, Ac-Met-Glu, Ac-Nle-Glu-, or Ac-Tyr-Glu-;
W is -His- or -D-His-;
X is -Phe-, -D-Phe-, -Tyr-, -D-Tyr-, or -(pNO$_2$)D-Phe$^7$-;
Y is -Arg- or -D-Arg-;
Z is -Trp- or -D-Trp-; and
R$_2$ is —NH$_2$; -Gly-NH$_2$; or -Gly-Lys-NH$_2$.

In another aspect, the alpha-MSH analogue may be selected from cyclic analogues which are disclosed in Australian Patent No. 618733 where an intramolecular interaction (such as a disulfide or other covalent bond) exists (1) between the amino acid residue at position 4 and an amino acid residue at position 10 or 11, and/or (2) between the amino acid residue at position 5 and the amino acid residue at position 10 or 11.

The alpha-MSH analogue may be a linear analogue as disclosed in U.S. Pat. No. 5,674,839, selected from the group consisting of:

Ac-Ser-Tyr-Ser-Nle-Glu-His-D-Phe-Arg-Trp-Lys-Gly-Pro-Val-NH$_2$

Ac-Ser-Tyr-Ser-Nle-Asp-His-D-Phe-Arg-Trp-Lys-Gly-Pro-Val-NH$_2$

Ac-Nle-Glu-His-D-Phe-Arg-Trp-Lys-Gly-Pro-Val-NH$_2$

Ac-Nle-Asp-His-D-Phe-Arg-Trp-Lys-Gly-Pro-Val-NH$_2$

Ac-Nle-Asp-His-D-Phe-Arg-Trp-Gly-NH$_2$

Ac-Nle-Glu-His-D-Phe-Arg-Trp-Lys-NH$_2$

Ac-Nle-Asp-His-D-Phe-Arg-Trp-Lys-NH$_2$

Ac-Nle-Glu-His-D-Phe-Arg-Trp-Orn-NH$_2$

Ac-Nle-Asp-His-D-Phe-Arg-Trp-Orn-NH$_2$

Ac-Nle-Glu-His-D-Phe-Arg-Trp-Dab-NH$_2$

Ac-Nle-Asp-His-D-Phe-Arg-Trp-Dab-NH$_2$

Ac-Nle-Glu-His-D-Phe-Arg-Trp-Dpr-NH$_2$

Ac-Nle-Glu-His-Phe-Arg-Trp-Lys-NH$_2$

Ac-Nle-Asp-His-Phe-Arg-Trp-Lys-NH$_2$

The alpha-MSH analogue may also be a cyclic analogue as disclosed in U.S. Pat. No. 5,674,839, selected from the group consisting of:

Ac-Nle-Glu-His-D-Phe-Arg-Trp-Lys-Gly-Pro-Val-NH$_2$

Ac-Nle-Glu-His-D-Phe-Arg-Trp-Lys-NH$_2$

Ac-Nle-Asp-His-D-Phe-Arg-Trp-Lys-NH$_2$

Ac-Nle-Asp-His-D-Phe-Arg-Trp-Orn-NH$_2$

Ac-Nle-Asp-His-D-Phe-Arg-Trp-Dab-NH$_2$

Ac-Nle-Asp-His-D-Phe-Arg-Trp-Dpr-NH$_2$

Ac-Ser-Tyr-Ser-Nle-Asp-His-D-Phe-Arg-Trp-Lys-Gly-Pro-Val-NH$_2$

Ac-Ser-Tyr-Ser-Nle-Asp-His-D-Phe-Arg-Trp-Lys-NH$_2$

Ac-Tyr-Ser-Nle-Asp-His-D-Phe-Arg-Trp-Lys-NH$_2$

Ac-Ser-Nle-Asp-His-D-Phe-Arg-Trp-Lys-NH$_2$

Ac-Nle-Asp-His-D-Phe-Arg-Trp-Lys-NH$_2$

Ac-Nle-Asp-His-D-Phe-Arg-Trp-Lys-Gly-NH$_2$

Ac-Nle-Asp-His-D-Phe-Arg-Trp-Lys-Gly-Pro-NH$_2$

Ac-Nle-Asp-His-D-Phe-Arg-Trp-Lys-Gly-Pro-Val-NH$_2$

-continued

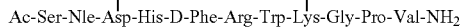

Ac-Ser-Nle-Asp-His-D-Phe-Arg-Trp-Lys-Gly-Pro-Val-NH$_2$

Where referred to herein, Ala=alanine, Arg=arginine, Dab=2,4-diaminobutyric acid, Dpr=2,3-diaminopropionic acid, Glu=glutamic acid, Gly=glycine, His=histidine, Lys=lysine, Met=methionine, Nle=norleucine, Orn=ornithine, Phe=phenylalanine, (pNO$_2$) Phe=paranitrophenylalanine, Plg=phenylglycine, Pro=proline, Ser=serine, Trp=tryptophan, TrpFor=N$^{1-}$formyl-tryptophan, Tyr=tyrosine, Val=valine. All peptides are written with the acyl-terminal end at the left and the amino terminal end to the right; the prefix "D" before an amino acid designates the D-isomer configuration, and unless specifically designated otherwise, all amino acids are in the L-isomer configuration.

In one aspect, the alpha-MSH analogue can be

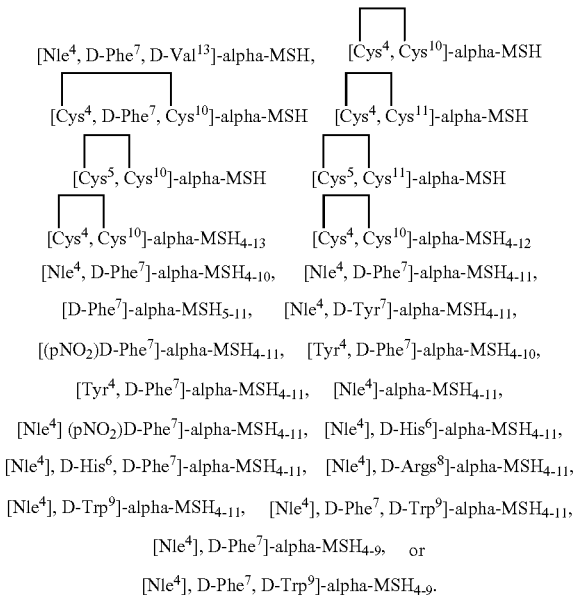

In one aspect, the alpha-MSH analogue is
[Nle$^4$, D-Phe$^7$]-alpha-MSH$_{4-10}$,
[Nle$^4$, D-Phe$^7$]-alpha-MSH$_{4-11}$,
[Nle$^4$, D-Phe$^7$, D-Trp$^9$]-alpha-MSH$_{4-11}$, or
[Nle$^4$, D-Phe$^7$]-alpha-MSH$_{4-9}$.

In a further aspect, the alpha-MSH analogue is [Nle$^4$, D-Phe$^7$]-alpha-MSH.

It will be appreciated that the actual preferred amounts of the alpha-MSH analogue in a specified case will vary according to the specific compounds being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining doses for inducing melanogenesis by the methods described herein. In one aspect, the alpha-MSH analogue is administered in an amount to induce melanogenesis without inducing homologous desensitization of the melanocortin-1 receptors of the subject. In another aspect, the alpha-MSH analogue is administered at a level not exceeding 10 ng/ml in the plasma of the subject for a period of at least 24 hours. In various other aspects, the alpha-MSH analogue is administered at a level not exceeding 9 ng/ml, 8 ng/ml, 7 ng/ml, 6 ng/ml, 5 ng/ml, 4 ng/ml, 3 ng/ml, 2 ng/ml, 1 ng/ml, 0.5 ng/ml, 0.2 ng/ml or 0.1 ng/ml, or lower, in the plasma of the subject for a period of at least 24 hours.

Any of the alpha-MSH analogues useful herein can be administered to a subject using a variety of administration or delivery techniques known in the art. It is desirable to maintain low concentrations of the alpha-MSH analogue in the plasma of the subject to induce melanogenesis in the subject. Therefore, the mode of administration will depend upon the subject to be treated and the alpha-MSH analogue selected. In various aspects, the alpha-MSH analogues can be administered orally or parenterally. The term "oral" is used herein to encompass administration of the compounds via the digestive tract. The term "parenteral" is used herein to encompass any route of administration, other than oral administration, by which the alpha-MSH analogue is introduced into the systemic circulation which includes, but is not limited to, intravenous, intramuscular, subcutaneous, intraperitoneal, intradermal, ocular, inhalable, rectal, vaginal, transdermal, topical, buccal, sublingual, or mucosal administration. The term "mucosal" as used herein encompasses the administration of the compounds by methods that employ the mucosa (mucous membranes) of the human body such as, but not limited to, buccal, intranasal, gingival, vaginal, sublingual, pulmonary, or rectal tissue. The term "transdermal" as used herein encompasses the administration of the compounds that go into the skin or go through the skin using formulations such as, but not limited to, transdermal formulations, buccal patches, skin patches, or transdermal patches. The term "topical" as used herein encompasses administration by applying conventional topical preparations such as creams, gels, or solutions for localized percutaneous delivery and/or by solution for systemic and/or localized delivery to areas such as, but not limited to the eye, skin, rectum, and vagina.

In one aspect, delivery systems composed of devices or compositions containing an alpha-MSH analogue can be manufactured that allow for the controlled-release, extended-release, modified-release, sustained-release, pulsatile-release, or programmed-release delivery of the alpha-MSH analogue in order to maintain low concentrations of the alpha-MSH analogue in the plasma of the subject. Depending on the delivery system or composition of a formulation or route of administration chosen, drugs or active pharmaceutical ingredients can be delivered for hours, weeks, or months following a single administration. Drug-delivery devices include, but are not limited to pumps, needle-free injectors, metered-dose inhalers, and the like. Transdermal compositions with or without penetration enhancers include but are not limited to transdermal patches, microneedles, and transdermal formulations that achieve drug delivery using inotophoresis, sonophoresis, electroporation, thermoporation, perfusion, adsorption and absorption. Other delivery systems include, but are not limited to, biodegradable or non-biodegradable rods or other shaped implants, fibers, microparticles, microspheres, microcapsules, nanospheres, nanocapsules, porous silicon nanoparticles, in situ gelling formulations, in situ bolus forming compositions, quick dissolving tablets and the like, buccal patches, films, tablets, capsules, osmotic pressure driven formulations, liquid filled capsules, liposomes and other lipid based compositions and the like, pegalation and the like, hydrogel formulations, emulsions, microemulsions, and suspensions.

In one aspect, polymeric delivery systems can be microparticles including, but not limited to microspheres, microcapsules, nanospheres and nanoparticles comprising biodegradable polymeric excipients, non-biodegradable polymeric excipients, or mixtures of polymeric excipients thereof, or the polymeric delivery systems can be, but not limited to rods or other various shaped implants, wafers, fibers, films, in situ forming boluses and the like comprising biodegradable polymeric excipients, non-biodegradable polymeric excipients, or mixtures thereof. These systems can be made from a single polymeric excipient or a mixture or blend of two or more polymeric excipients.

A suitable polymeric excipient includes, but is not limited to, a poly(diene) such as poly(butadiene) and the like; a polyalkene) such as polyethylene, polypropylene, and the like; a poly(acrylic) such as poly(acrylic acid) and the like; a poly(methacrylic) such as poly(methyl methacrylate), a poly(hydroxyethyl methacrylate), and the like; a poly(vinyl ether); a poly(vinyl alcohol); a poly(vinyl ketone); a poly (vinyl halide) such as poly(vinyl chloride) and the like; a poly(vinyl nitrile), a poly(vinyl ester) such as poly(vinyl acetate) and the like; a poly(vinyl pyridine) such as poly(2-vinyl pyridine), poly(5-methyl-2-vinyl pyridine) and the like; a poly(styrene); a poly(carbonate); a poly(ester); a poly(orthoester) including a copolymer, a poly(esteramide); a poly(anhydride); a poly(urethane); a poly(amide); a cellulose ether such as methyl cellulose, hydroxyethyl cellulose, hydroxypropyl methyl cellulose, and the like; a cellulose ester such as cellulose acetate, cellulose acetate phthalate, cellulose acetate butyrate, and the like; a poly (saccharide), a protein, gelatin, starch, gum, a resin, and the like. These materials may be used alone, as physical mixtures (blends), or as co-polymers. Derivatives of any of the polymers listed above are also contemplated.

In one aspect, the polymeric excipient of the delivery system includes a biocompatible, non-biodegradable polymer such as, for example, a silicone, a polyacrylate; a polymer of ethylene-vinyl acetate; an acyl substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; or a blend or copolymer thereof.

In another aspect, the polymeric excipient includes a biocompatible, biodegradable polymer such as, for example, a poly(lactide); a poly(glycolide); a poly(lactide-co-glycolide); a poly(lactic acid); a poly(glycolic acid); a poly (lactic acid-co-glycolic acid); a poly(caprolactone); a poly (orthoester); a poly(phosphazene); a poly(hydroxybutyrate) or a copolymer containing a poly(hydroxybutarate); a poly (lactide-co-caprolactone); a polycarbonate; a polyesteramide; a polyanhydride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer, or a blend or copolymer thereof.

In one aspect, the delivery system comprises an implant or rod, wherein the implant or rod comprises a biodegradable polymer, wherein the alpha-MSH analogue is imbedded within the implant or rod. In one aspect, the alpha-MSH analogue is encapsulated in an implant or rod composed of poly(lactide-co-glycolide), poly(lactide), poly(glycolide), or a mixture thereof. Lactide/glycolide polymers for drug-delivery formulations are typically made by melt polymerization through the ring opening of lactide and glycolide monomers. Some polymers are available with or without carboxylic acid end groups. When the end group of the poly(lactide-co-glycolide), poly(lactide), or poly(glycolide) is not a carboxylic acid, for example, an ester, then the resultant polymer is referred to herein as blocked or capped. The unblocked polymer, conversely, has a terminal carboxylic group. In one aspect, linear lactide/glycolide polymers are used; however star polymers can be used as well. In certain aspects, high molecular weight polymers can be used for medical devices, for example, to meet strength requirements. In other aspects, low molecular weight polymers can be used for drug-delivery and vaccine delivery products where resorption time and not material strength is as important. The lactide portion of the polymer has an asymmetric carbon. Commercially racemic DL-, and D-polymers are available. The L-polymers are more crystalline and resorb slower than DL-polymers. In addition to copolymers comprising glycolide and DL-lactide or L-lactide, copolymers of L-lactide and DL-lactide are available. Additionally, homopolymers of lactide or glycolide are available.

In the case when the biodegradable polymer is poly (lactide-co-glycolide), poly(lactide), or poly(glycolide), the amount of lactide and glycolide in the polymer can vary. In one aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In one aspect, the biodegradable polymer can be poly(lactide), 85:15 poly(lactide-co-glycolide), 75:25 poly(lactide-co-glycolide), or 65:35 poly(lactide-co-glycolide) where the ratios are mole ratios.

In one aspect, when the biodegradable polymer is poly (lactide-co-glycolide), poly(lactide), or poly(glycolide), the polymer has an intrinsic viscosity of from 0.15 to 1.5 dL/g, 0.25 to 1.5 dL/g, 0.25 to 1.0 dL/g, 0.25 to 0.8 dL/g, 0.25 to 0.6 dL/g, or 0.25 to 0.4 dL/g as measured in chloroform at a concentration of 0.5 g/dL at 30° C.

The amount of alpha-MSH analogue that is encapsulated or incorporated in the biodegradable polymer will vary depending upon the selection of the biodegradable polymer, the encapsulation or incorporation technique, and the amount of alpha-MSH to be delivered to the subject. In one aspect, the amount of alpha-MSH analogue encapsulated in the microcapsule, implant, or rod can be up to 50% by weight of the delivery system. In other aspects, the amount of alpha-MSH analogue encapsulated in the microcapsule, implant, or rod can be from 5 to 60, 10 to 50%, 15 to 40%, or 15 to 30% by. weight of the delivery system.

In another aspect, where the alpha-MSH analogue is delivered by another delivery system such as a transdermal formulation, the amount of alpha-MSH analogue in the formulation can be from 0.001 to 10%, or 0.05 to 5% by weight of the formulation.

Other pharmaceutically-acceptable components can be encapsulated or incorporated in the delivery system in combination with the alpha-MSH analogue. For example, the pharmaceutically-acceptable component can include, but is not limited to, a fatty acid, a sugar, a salt, a water-soluble polymer such as polyethylene glycol, a protein, polysaccharride, or carboxmethyl cellulose, a surfactant, a plasticizer, a high- or low-molecular-weight porosigen such as polymer or a salt or sugar, or a hydrophobic low-molecular-weight compound such as cholesterol or a wax. In another aspect, the delivery system comprises an implant or rod, wherein the alpha-MSH analogue is [Nle$^4$, D-Phe$^7$]-alpha-MSH in the amount from 15% to 45% by weight of the implant or rod, wherein the rod or implant comprises poly(lactide) or poly(lactide-co-glycolide) such as, for example, 85:15 poly(lactide-co-glycolide).

Any of the delivery systems described herein can be administered using techniques known in the art. In one aspect, the delivery system can be administered subcutaneously to the subject. In this aspect, the duration of administration can vary depending upon the amount of alpha-MSH analogue that is encapsulated and the biodegradable polymer selected. In one aspect, the delivery system is administered subcutaneously to the subject and releases the alpha-MSH analogue for a period of at least 1, 2, 4, 6, 8, 10 or 12 days. In one aspect, the delivery system releases the alpha-MSH analogue in the subject for up to three months. In various other aspects, the delivery system releases the alpha-MSH analogue in the subject for 5 days, 10 days, 15 days, 20 days, 25 days, or 30 days.

In one aspect, any of the alpha-MSH analogues can be combined with at least one pharmaceutically-acceptable carrier to produce a pharmaceutical composition. The pharmaceutical compositions can be prepared using techniques known in the art. In one aspect, the composition is prepared by admixing the alpha-MSH analogue with a pharmaceutically-acceptable carrier. The term "admixing" is defined as mixing the two components together so that there is no chemical reaction or physical interaction. The term "admixing" also includes the chemical reaction or physical interaction between the alpha-MSH analogue and the pharmaceutically-acceptable carrier.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for administration include sterile aqueous or non-aqueous solutions, suspensions, and emulsions. Examples of non-aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, ointments, suppositories, sprays, liquids and powders. Conventional pharmaceutical carriers, aqueous, powder or oily bases, thickeners and the like may be necessary or desirable. The alpha-MSH analogue can be admixed under sterile conditions with a physiologically acceptable carrier and any preservatives, buffers, propellants, or absorption enhancers as may be required or desired. Reference is made to documents cited herein, e.g., U.S. Pat. No. 5,990,091, WO 98/00166, and WO 99/60164, for the preparation of compositions for topical applications, e.g., viscous compositions that can be creams or ointments, as well as compositions for nasal and mucosal administration.

In the case when the composition is administered mucosally, ocularly, intranasally, or by inhalation, the formulation can be in the form of a drop, a spray, an aerosol, or a sustained release format. The spray and the aerosol can be achieved through use of the appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California; Joshi, A., S. Ping and K. J. Himmelstein, Patent Application WO 91/19481). These systems maintain prolonged drug contact with the absorptive surface preventing washout and nonproductive drug loss.

The methods described herein induce melanogenesis in a subject (i.e, increase melanin production from melanin-producing cells). The methods herein increase melanin production without inducing homologous desensitization of the melanocortin-1-receptors of the subject. By maintaining low concentrations of the alpha-MSH analogue in the plasma of the subject, it is possible to increase melanin production without inducing homologous desensitization of the melanocortin-1-receptors of the subject, which can prevent the occurrence of skin damage in a subject due to exposure to UV radiation. In one aspect, described herein are methods for preventing UV radiation-induced skin damage in a human subject comprising administering to the subject an alpha-MSH analogue, wherein the alpha-MSH analogue is administered at a level to induce melanogenesis in the subject without inducing homologous desensitization of the melanocortin-1-receptors of the subject. In another aspect, described herein are methods for preventing UV radiation-induced skin damage in a human subject comprising administering to the subject an alpha-MSH analogue, wherein the alpha-MSH analogue is administered at a level not exceeding 10 ng/ml in the plasma of the subject for a period of at least 24 hours.

In yet another aspect, described herein are compositions for preventing UV radiation-induced skin damage in a human subject, wherein the composition administers an alpha-MSH analogue to the subject in an effective amount and time to induce melanogenesis by the melanocytes in epidermal tissue of the subject without inducing homologous desensitization of the melanocortin-1 receptors of the subject. In a further aspect, described herein are compositions for preventing UV radiation-induced skin damage in a human subject, wherein the composition administers an alpha-MSH analogue to the subject at a level not exceeding 10 ng/ml in the plasma of the subject for a period of at least 24 hours.

In one aspect, an epidermal cell can be contacted with the alpha-MSH analogue in order to prevent UV radiation-induced skin damage in a subject. In these aspects, the epidermal cell can be contacted with the alpha-MSH analogue in vivo, in vitro, or ex vivo

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, component mixtures, desired solvents, solvent mixtures, temperatures, pressures and other reaction ranges and conditions that can be used to optimize the product purity and yield obtained from the described process. Only reasonable and routine experimentation will be required to optimize such process conditions.
I. Preparation of Formulations Example 1

Fabrication of Implants Containing 20 mg of Melanotan

[Nle$^4$-D-Phe$^7$]-α-MSH, (Melanotan; MT-1), is the medication involved in the studies described below. The substitution of amino acids at positions 4 and 7 makes this analogue 10-1000 times more active than α-MSH in one or more bioassays.[7] An implant formulation was made for Study 3 with Melanotan and poly(DL-lactide). The poly(DL-lactide) had an inherent viscosity of 0.37 dL/g. The inherent viscosity was measured at 30° C. with 0.5 gm/dL polymer concentration in chloroform.

The desired Melanotan content in the implant was 35 wt % Melanotan peptide. Therefore, Melanotan (36 g, where 78% is Melanotan peptide) and the poly(DL-lactide) (44 g) were dry blended using a mortar and pestle to form a blended powder.

Next a Tinius Olsen (MP 600) melt plastometer was used to melt extrude the blended powder. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a 3.9-mm die was used, meaning that the core of the die was 3.9 mm in diameter. The main block of the Tinius Olsen has heater bands encased by insulation and a shroud that allow the Tinius Olsen to be heated to a desired temperature. A thermocouple was used to measure the temperature of the block. The control system then uses the thermocouple values to either turn the heater bands on or off. Throughout the extrusion process, the heater bands will switch off and on to maintain the desired temperature. Once the blend was loaded into the Tinius Olsen, a charging rod was placed in the core or the Tinius Olsen to compress the blend. Weights were placed on the end of the charging rod as appropriate. More specifically, the Tinius Olsen was equilibrated to 90° C. The compression load used, while the blend was melting, was 3,700 grams. The equilibration time for the blend to melt lasted for about 15 minutes. The plug was removed from the discharge area and the extrusion load of 12,360 grams was added, which included the compression load. An extruded rod of approximately 140-180 cm was then made.

Ten 10 samples (about 55 mg each) were selected for potency testing (Melanotan content). The potency test determined that the extruded rod contained 34.19 wt % Melanotan. Knowing the Melanotan content, the extruded rods were then cut into lengths to afford implants with about 20 mg Melanotan peptide in each implant.

Next about 30 mL of ethyl acetate were placed in a small beaker. Each implant was affixed to a needle point holding device and dipped in the ethyl acetate for about 5 seconds. The implants were then "dried" at room conditions.

The in vitro release characteristics of similar Melanotan implants made with poly(DL-lactide) by the above-described manufacturing process are shown in FIG. 1. The Melanotan content was 36 wt %. The release data showed that the implants released Melanotan for up to 21 days.

Example 2

Preparation of Implants with Different Lactide/glycolide Polymers

Several Melanotan implants were made essentially by the extrusion process described in Example 1. However, the properties of the implants varied with respect to:
Lactide/glycolide ratio of the polymer
Polymer end group
Polymer inherent viscosity
Melanotan content
Table 1 lists representative examples of the different implants prepared.

TABLE 1

| Run No. | Lactide/ Glycolide (mole ratio) | Inherent viscosity (dL/gm) | Polymer end group | Melanotan content (wt %) |
|---|---|---|---|---|
| 1$^a$ | 100:0 | 0.37 | Capped | 36.0 |
| 2 | 100:0 | 0.67 | Capped | 29.2 |
| 3 | 100:0 | 1.09 | Capped | 26.9 |
| 4 | 85:15 | 0.36 | COOH | 20.8 |
| 5 | 85:15 | 0.36 | COOH | 17.4 |
| 6 | 85:15 | 0.36 | COOH | 17.3 |
| 7 | 75:25 | 0.44 | Capped | 15.0 |
| 8 | 75:25 | 0.44 | Capped | 16.9 |
| 9 | 65:35 | 0.42 | Capped | 16.7 |

$^a$Solvent treated

Figure 2:
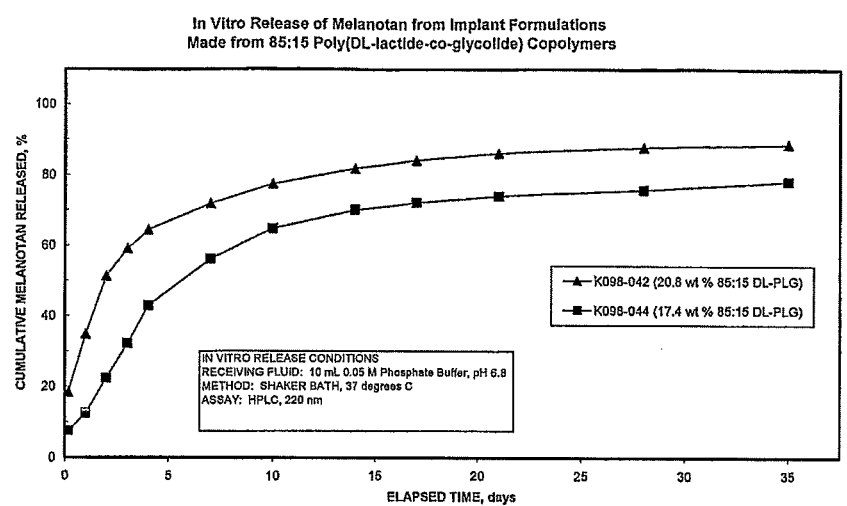
FIG. 2 shows the in vitro release of Melanotan from implant formulations made from 85:15 poly-(D,L-lactide-co-glycolide) copolymers.

In summary, the polymers for the above implants ranged from homopolymers (poly(DL-lacide)) to copolymers of lactide and glycolide. Therefore, polymers with 100 mole % lactide to 65 mole % lactide were used. The end groups of these polymers were capped (blocked) or were synthesized to have carboxylic acid end groups. The inherent viscosity of the polymers ranged from 0.36 to 1.09 dL/g. The inherent viscosities were determined with polymers dissolved in chloroform at a concentration of 0.5 gm/dL. The viscosity measurements were made at 30° C. The Melanotan content of the implants ranged from 15 to 45 wt %. The typical in vitro release characteristics of the Melanotan implants made with 85:15 poly(DL-lactide-co-glycolide) in runs 4 and 5 are shown in FIG. 2.

Example 3

Fabrication of Implants Containing 5 mg of Melanotan

An implant formulation was made with Melanotan and 84:16 poly(DL-lactide-co-glycolide) with carboxylic acid end groups. The poly(DL-lactide-co-glycolide) had an inherent viscosity of 0.29 dL/g. The inherent viscosity was measured at 30° C. with 0.5 gm/dL polymer concentration in chloroform.

The desired Melanotan content in the implant was 17.3 wt % Melanotan peptide. Therefore, Melanotan (3 g) and the poly(DL-lactide) (12 g) were dry blended using a mortar and pestle to form a blended powder. The 3 gm of Melanotan comprised about 88% Melanotan peptide.

Next a Tinius Olsen (MP 600) melt plastometer was used to melt extrude the blended powder. The Tinius Olsen is a solid block of steel about 80 mm in diameter and about 160 mm high/long with a hollow core about 13 mm in diameter. The discharge of the core has a shoulder that allows different size "dies" to be used based on the desired diameter of extruded rod. For this run, a 1.5-mm die was used, meaning that the core of the die was 1.5 mm in diameter. The main block of the Tinius Olsen has heater bands encased by insulation and a shroud that allow the Tinius Olsen to be heated to a desired temperature. A thermocouple was used to measure the temperature of the block. The control system then used the thermocouple values to either turn the heater bands on or off. Throughout the extrusion process the heater bands will switch off and on to maintain the desired temperature. Once the blend was loaded into the Tinius Olsen, a charging rod was placed in the core or the Tinius Olsen to compress the blend. Weights were placed on the end of the charging rod as appropriate. More specifically, the Tinius Olsen was equilibrated to 87° C. The compression load used, while the blend was melting, was 3,700 grams. The equilibration time for the blend to melt lasted for about 15 minutes. The plug was removed from the discharge area and the extrusion load of 10,300 grams was added (includes the compression load). An extruded rod approximately 600-700 cm was then made.

Figure 3:
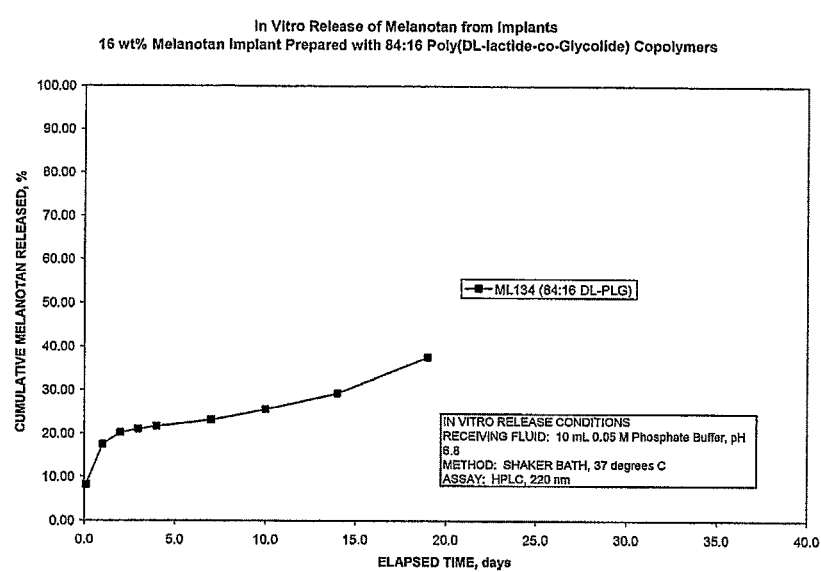
FIG. 3 shows the in vitro release of Melanotan from implant formulations made from 84:16 poly-(D,L-lactide-co-glycolide) copolymers.

Ten 10 samples (about 30 mg each) were selected for potency testing (Melanotan content). The potency test determined that the extruded rod contained 16.08 wt % Melanotan. Knowing the Melanotan content, the extruded rods were then cut into lengths to afford implants with about 5 mg Melanotan peptide in each implant. The in vitro release characteristics of similar Melanotan implants made with 84:16 poly(DL-lactide-co-glycolide)) by the above-described manufacturing process are shown in FIG. 3. The Melanotan content is 16 wt %. These release data showed that the implants released Melanotan for at least 21 days.

II. In Vivo Testing

Example 4

Clinical Trials

Four clinical trials were conducted using different means of delivering of Melanotan (MT-1). In the first clinical trial, a double-blind, randomized, placebo-controlled clinical trial was conducted with 16 human subjects, later reduced to 15 subjects. Melanotan (MT-1) was administered at a fixed, subcutaneous daily dose for 10 consecutive days to 12 subjects, and the remaining 4 subjects were administered the placebo (saline). One subject (Melanotan) did not complete the trial protocol. Average baseline melanin density (MD) and MD change (%) was measured in all 11 protocol completers. In the second clinical trial, a double-blind, randomized, placebo-controlled clinical trial was conducted with 81 human subjects, later reduced to 79 subjects. Melanotan (MT-1) was administered at a fixed, subcutaneous daily dose for 30 days over a 70 day period to 59 subjects, and the remaining 20 subjects were administered the placebo (saline). Fourteen subjects did not complete the trial protocol (twelve Melanotan and two placebo). Average baseline melanin density (MD) and MD change (%) was measured in all 47 protocol completers. In the third clinical trial, a dose-escalation study of a single depot controlled release formulation was conducted with 3 human subjects. Melanotan (MT-1) was administered as a single, subcutaneous controlled release dose at day 1 only. Average baseline melanin density (MD) and MD change (%) was measured in these three subjects. In the fourth clinical trial, a dose-escalation study of a single depot controlled release formulation was conducted with 12 human subjects. Melanotan (MT-1) was administered as a single, subcutaneous controlled release dose at day 1 only. Average baseline melanin density (MD) and MD change (%) was measured in these twelve subjects.

The results of these trials show that the MD change (%) of the subjects of Studies 3 and 4 was dramatically higher and quicker than for the subjects of Studies 1 and 2, notwithstanding the fact that the subjects of Studies 3 and 4 received a substantially lower amount of Melanotan overall when compared with the subjects of Studies 1 and 2.

a. Primary Objective

Study 1:

One of the primary objectives of this study was to determine the pharmacokinetics of 0.16 mg/kg/day of Melanotan administered by subcutaneous injection on 10 consecutive days to healthy adult subjects.

Study 2:

One of the primary objectives of this study was to compare the incidence of sunburn cells (defined as apoptotic cells) in all subjects elicited 24 hours after controlled solar irradiation (3×MED) to a small area of skin (2×2 cm) at baseline and 90 days after initiation of dosing with Melanotan or placebo.

Studies 3 and 4:

One of the primary objectives of this study was to determine the pharmacokinetics of increasing doses of a single depot injection of Melanotan administered subcutaneously to healthy adult subjects.

b. Secondary Objective

To establish the safety and tolerability (defined as absence of any toxicities ≥Grade 3 by WHO-CTC) of a course of Melanotan (MT-1) given as either a course of 10 consecutive daily liquid injections at a fixed subcutaneous dose of 0.16 mg/Kg/day in Caucasian subjects (study 1), or 3 (10 day; 5 days a week×2 weeks) monthly courses of Melanotan (MT-1) at a fixed subcutaneous dose of 0.16 mg/Kg/day in Caucasian subjects (study 2), or as a single depot injection of Melanotan (MT-1) in Caucasian subjects (Studies 3 and 4).

c. Primary Efficacy Objective (for all four studies)
Degree of Tanning

To compare the degree of tanning at 8 anatomic sites (determined by serial reflectance changes) at set periods after initiation of dosing with Melanotan and placebo in Caucasian subjects.

A. Testing Protocol

1. Selection of Study Population

The target population was male and female Caucasian subjects. The following inclusion and exclusion criterion had to be met by each subject before enrollment in the study. The inclusion and exclusion criterion was similar for all three studies conducted.

Inclusion Criteria
  Male and Female Caucasian Subjects (skin types I to IV on the Fitzpatrick scale[16])
  Age 18-65 years
  Weight ≤85 Kg
  Free of significant abnormal findings as determined by medical history (including family history), physical examination, haematology, plasma biochemistry and vital signs (blood pressure, pulse rate) determined at screening
  Written informed consent prior to the performance of any study-specific procedures 2. Study Medication 2.1 Description of Study Medication For Studies 1 and 2, Melanotan was provided in single-use sterile 6 mL vials each containing 16 mg/mL of Melanotan dissolved in 1 mL sterile saline for injection. Placebo vials were identical and contained 1 mL sterile saline for injection. For Studies 3 and 4, Melanotan was provided in biodegradable rods.

2.2 Dosage and Administration of Study Medication

For Study 1:

Active: Melanotan was provided in single-use, sterile 6 mL vials each containing 16 mg (±5%) of Melanotan in 1 mL sterile saline. A dose of 0.16 mg/kg/day was administered by subcutaneous injection to each subject receiving the Melanotan treatment, which is equivalent to a dose volume of 0.01 mL/kg/day.

Placebo: Placebo was provided as single-use, sterile 6 mL vials containing 1 mL sterile saline. A dose volume of 0.01 mL/kg/day was subcutaneously injected at each administration.

The treatments were injected subcutaneously, using a 25-gauge needle (16 mm length) and 1 mL syringe, to the abdomen each day for 10 consecutive days. Each subject's body weight was determined at check-in and the same weight was used for all dose calculations for subsequent treatments. Each subject received, in total, 1.6 mg/kg of Melanotan, which equates to 112 mg of Melanotan for a 70 kg person.

For Study 2:

Active: Melanotan was provided in single-use, sterile 6 mL vials each containing 16 mg (±5%) of Melanotan in 1 mL sterile saline. A dose of 0.16 mg/kg/day was administered by subcutaneous injection to each subject receiving the Melanotan treatment, which is equivalent to a dose volume of 0.01 mL/kg/day.

Placebo: Placebo was provided as single-use, sterile 6 mL vials containing 1 mL sterile saline. A dose volume of 0.01 mL/kg/day was subcutaneously injected at each administration.

The treatments were injected subcutaneously, using a 25 gauge needle (16 mm length) and 1 mL syringe, to the abdomen each day for 5 days a week×2 weeks. Each subject's body weight was determined at check-in and the same weight was used for all dose calculations for the first 10 days treatment. This cycle of treatment was repeated at Days 29 to 40 and Days 57 to 66. The subject was reweighed at the start of each dosing period for calculation of dose. Drug was given as nearly as possible at the same time each day (+/−4 hours). Each subject received, in total, 4.8 mg/kg of Melanotan, which equates to 336 mg of Melanotan for a 70 kg person.

For Study 3:

Active: Melanotan was provided in a biodegradable poly (DL-lactide) rod containing 20 mg (±10%) of Melanotan. A single dose of 20 mg was administered by subcutaneous implantation to each subject.

The treatments were implanted subcutaneously, using a trocar delivery device (5.2 mm ID×70 mm length), in the abdomen on Day 1 only. Each subject received, in total, 0.29 mg/kg of Melanotan, which equates to 20 mg of Melanotan for a 70 kg person.

For Study 4:

Active: Melanotan was provided in a biodegradable poly (DL-lactide-co-glycolide) rod containing 5 mg (±10%) of Melanotan. Doses of 10 and 20 mg were administered by subcutaneous implantation to each subject.

The treatments were implanted subcutaneously, using a SURFLO® I.V. catheter with a 16G needle, in the inner upper arm on Day 1 only.

2.3 Use of sunscreen products:

All subjects were advised to apply SPF 25+ sunscreen to exposed skin whenever they expected to be in the sun for prolonged periods of time. Normal daily activity did not require extra precautions.

3. Study Procedures 3.1 Measurement of Primary Objective

For Study 1:

Blood collection was performed at 0 hr (time of treatment) and 0.5, 1, 2, 3, 4, 6, 8, 10, 16 and 24 hr post-treatment on Day 1 and Day 10 of the study for pharmacokinetic analysis after dose administration. Subject plasma samples were analysed for Melanotan using a validated LC/MS/MS method.

For Study 2:

On Day −7 to −2, subjects had their MED (minimal erythema dose) determined, received controlled UV radiation at 3.0 times their MED, and skin blister biopsy specimens were collected the following day. On Day 89, subjects received controlled UV radiation at 3.0 times their IVIED, and skin blister biopsy specimens were collected the following day. Change in the number of sunburn (apoptotic) cells/100 cells, of epidermis resulting from 3×MED exposure from the beginning to the end of the study period as determined by light microscopy, was calculated.

For Study 3:

Blood collection was performed at Day 0 (time of treatment) and Day 2, 4, 6, 8, 10, 12, 15, 18, 21 and 25 post-implantation for pharmacokinetic analysis after dose administration. Subject plasma samples were analysed for Melanotan using a validated LC/MS/MS method.

For Study 4:

Blood collection was performed at Day 0 (time of treatment) and Day 1, 2, 3, 4, 6, 8, 10, 12, 15, 20 and 25 post-implantation for pharmacokinetic analysis after dose administration. Subject plasma samples were analysed for Melanotan using a validated LC/MS/MS method.

3.2 Measurement of Primary Efficacy Variables
Skin Reflectance—Degree of Tanning & Melanin Density (MD)
For Study 1:

Before treatment (Day 0), Day 9 and at Day 30, subjects had their skin pigmentation measured by a non-invasive quantitative skin chromaticity (reflectance) reading. Reflectance by the skin of wavebands of light measured at 20-nm intervals in the wavelength range 400-700 nm was recorded using a Minolta 508i spectrophotometer at eight skin sites (forehead, cheeks, neck, scapula, inner upper arm, forearm, abdomen and calf). The spectrophotometer was programmed to take three separate measurements at each site at each session to minimize error. A diagram for each subject was provided at baseline and measurements positions for all eight skin sites at baseline were recorded on this diagram. Subsequent repeat measurements were done with reference to the initial diagram to ensure they were taken as close as possible to the original measurement at each skin site.

At each visit the mean of the 3 separate measurements taken at each site for the reflectance values at 400 and 420 nm were obtained and recorded. Using the measurement of reflectance at 420 nm minus that at 400 nm a reasonable prediction of the melanin content of the skin was obtained, as described by Dwyer et al.[28]

The equation used was MD=100×(0.035307+0.009974 ($R_{420}$−$R_{400}$)) where MD is an estimate of the percentage of the epidermis of the skin that contains melanin, $R_{400}$ and $R_{420}$ denote reflectance at 400 nm and 420 nm, respectively. These MD measurements were calculated at the analysis stage.

For Study 2:

Before treatment (Day 0), Day 12, Day 30, Day 40, Day 60 and Day 90, subjects had their skin pigmentation measured by a non-invasive quantitative skin chromaticity (reflectance) reading. Reflectance by the skin of wavebands of light measured at 20-nm intervals in the wavelength range 400-700 nm was recorded using a Minolta 508i spectrophotometer at eight skin sites (forehead, cheeks, neck, scapula, inner upper arm, forearm, abdomen and calf). The spectrophotometer was programmed to take three separate measurements at each site at each session to minimize error. A diagram for each subject was provided at baseline and measurements positions for all eight skin sites at baseline were recorded on this diagram. Subsequent repeat measurements were done with reference to the initial diagram to ensure they were taken as close as possible to the original measurement at each skin site.

At each visit the mean of the 3 separate measurements taken at each site for the reflectance values at 400 and 420 nm were obtained and recorded. Using the measurement of reflectance at 420 nm minus that at 400 nm a reasonable prediction of the melanin content of the skin was obtained, as described by Dwyer et al.[28]

The equation used was MD=100×(0.035307+0.009974 ($R_{420}$−$R_{400}$)) where MD is an estimate of the percentage of the epidermis of the skin that contains melanin, $R_{400}$ and $R_{420}$ denote reflectance at 400 nm and 420 nm, respectively. These MD measurements were calculated at the analysis stage.

For Study 3:

Before treatment (Day 0), Day 10, Day 21, Day 30 and Day 60, subjects had their skin pigmentation measured by a non-invasive quantitative skin chromaticity (reflectance) reading. Reflectance by the skin of wavebands of light measured at 20-nm intervals in the wavelength range 400-700 nm was recorded using a Minolta 508i spectrophotometer at eight skin sites (forehead, cheeks, neck, scapula, inner upper arm, forearm, abdomen and calf). The spectrophotometer was programmed to take three separate measurements at each site at each session to minimize error. A diagram for each subject was provided at baseline and measurements positions for all eight skin sites at baseline were recorded on this diagram. Subsequent repeat measurements were done with reference to the initial diagram to ensure they were taken as close as possible to the original measurement at each skin site.

At each visit the mean of the 3 separate measurements taken at each site for the reflectance values at 400 and 420 nm were obtained and recorded. Using the measurement of reflectance at 420 nm minus that at 400 nm a reasonable prediction of the melanin content of the skin was obtained, as described by Dwyer et al.[28]

The equation used was MD=100×(0.035307+0.009974 ($R_{420}$−$R_{400}$) where MD is an estimate of the percentage of the epidermis of the skin that contains melanin, $R_{400}$ and $R_{420}$ denote reflectance at 400 nm and 420 nm, respectively. These MD measurements were calculated at the analysis stage.

For Study 4:

Before treatment (Day 0), Day 4, Day 10, Day 20, Day 30 and Day 60, subjects had their skin pigmentation measured by a non-invasive quantitative skin chromaticity (reflectance) reading. Reflectance by the skin of wavebands of light measured at 20-nm intervals in the wavelength range 400-700 nm was recorded using a Minolta 508i spectrophotometer at eight skin sites (forehead, cheeks, neck, scapula, inner upper arm, forearm, abdomen and calf). The spectrophotometer was programmed to take three separate measurements at each site at each session to minimize error. A diagram for each, subject was provided at baseline and measurements positions for all eight skin sites at baseline were recorded on this diagram. Subsequent repeat measurements were done with reference to the initial diagram to ensure they were taken as close as possible to the original measurement at each skin site.

At each visit the mean of the 3 separate measurements taken at each site for the reflectance values at 400 and 420 nm were obtained and recorded. Using the measurement of reflectance at 420 nm minus that at 400 nm a reasonable prediction of the melanin content of the skin was obtained, as described by Dwyer et al.[28]

The equation used was MD=100×(0.035307+0.009974 ($R_{420}$−$R_{400}$)) where MD is an estimate of the percentage of the epidermis of the skin that contains melanin, $R_{400}$ and $R_{420}$ denote reflectance at 400 nm and 420 nm, respectively. These MD measurements were calculated at the analysis stage.

4. Data Analysis
4.1 Efficacy Assessment
Primary Efficacy Objective
For Study 1:

Change in tanning from baseline (Day 0) to day 30, across 8 anatomic sites (forehead, cheeks, neck, scapula, inner upper arm, forearm, abdomen and calf), as determined by melanin density (MD) from skin reflectance measurements [Dwyer et al.[28]; MD=100×(0.035307+0.009974 (R420−R400)] was calculated.

For Study 2:

Change in tanning from baseline (Day 0) to day 90, across 8 anatomic sites (forehead, cheeks, neck, scapula, inner upper arm, forearm, abdomen and calf), as determined by melanin density (MD) from skin reflectance measurements [Dwyer et al.[28]; MD=100×(0.035307+0.009974 (11420−R400)] was calculated.

For Studies 3 and 4:

Change in tanning from baseline (Day 0) to day 60, across 8 anatomic sites (forehead, cheeks, neck, scapula, inner upper arm, forearm, abdomen and calf), as determined by melanin density (MD) from skin reflectance measurements [Dwyer et al. 28; MD=100×(0.035307+0.009974 (R420−R400)] was calculated.

B. Results

The following Tables 2, 3 and 4 list the responses of the protocol completers in Studies 1, 3 and 4 respectively in terms of the measured concentration of Melanotan in their plasma.

TABLE 2

Melanotan Plasma Concentrations (ng/mL) at Day 1 and 10 for Study 1.

| | Time (hr:min) post-treatment | | | | | | | | | | |
|---|---|---|---|---|---|---|---|---|---|---|---|
| | 0:00 | 0:30 | 1:00 | 2:00 | 3:00 | 4:00 | 6:00 | 8:00 | 10:00 | 16:00 | 24:00 |
| Day 1 | 0 | 105 | 41.4 | 9.64 | 2.07 | 0.76 | 0 | 0 | 0 | 0 | 0 |
| Day 10 | 0 | 100 | 48.1 | 11.3 | 2.9 | 0.28 | 0 | 0 | 0 | 0 | 0 |
| Mean | 0 | 103 | 44.8 | 10.5 | 2.5 | 0.52 | 0 | 0 | 0 | 0 | 0 |

TABLE 3

Melanotan Plasma Concentrations (ng/mL) for Study 3
Time (Day) post-treatment

| 0 | 2 | 4 | 6 | 8 | 10 | 12 | 15 | 18 | 21 | 25 |
|---|---|---|---|---|---|---|---|---|---|---|
| 0 | 1.39 | 0.41 | 0.17 | 0.12 | 0.06 | 0.15 | 0.03 | 0 | 0.01 | 0 |

TABLE 4

Melanotan Plasma Concentrations (ng/mL) for Study 4

| Dose (mg) | Time (Day) post-treatment | | | | | | | | | |
|---|---|---|---|---|---|---|---|---|---|---|
| | 0 | 1 | 2 | 3 | 4 | 6 | 8 | 10 | 12 | 15 | 20 |
| 10 | 0 | 0.21 | 0.04 | 0.05 | 0.03 | 0.00 | 0.01 | 0.01 | 0.01 | 0.02 | 0.01 |
| 20 | 0 | 0.58 | 0.21 | 0.11 | 0.08 | 0.04 | 0.04 | 0.04 | 0.05 | 0.04 | 0.04 |

Figure 4:
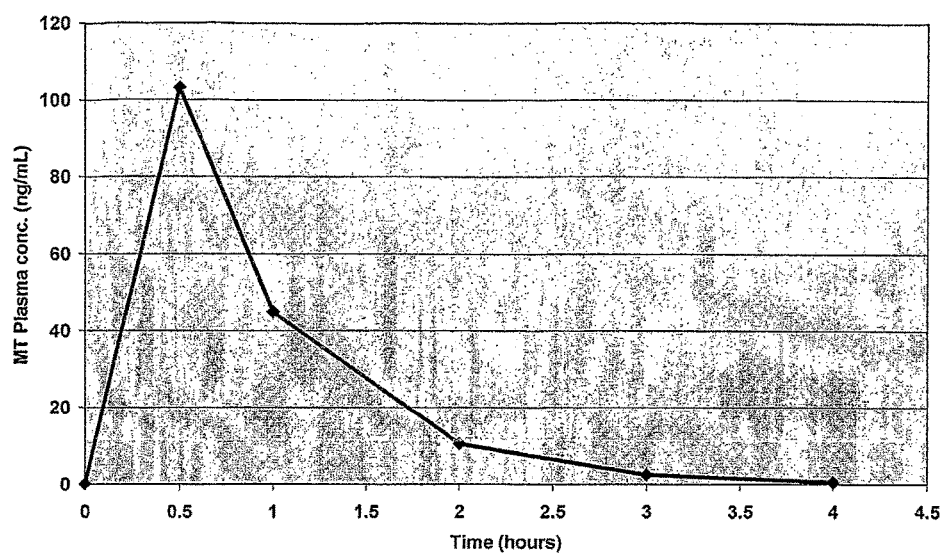
FIG. 4 shows the pharmacokinetic data from Study 1 described herein.
Figure 5:
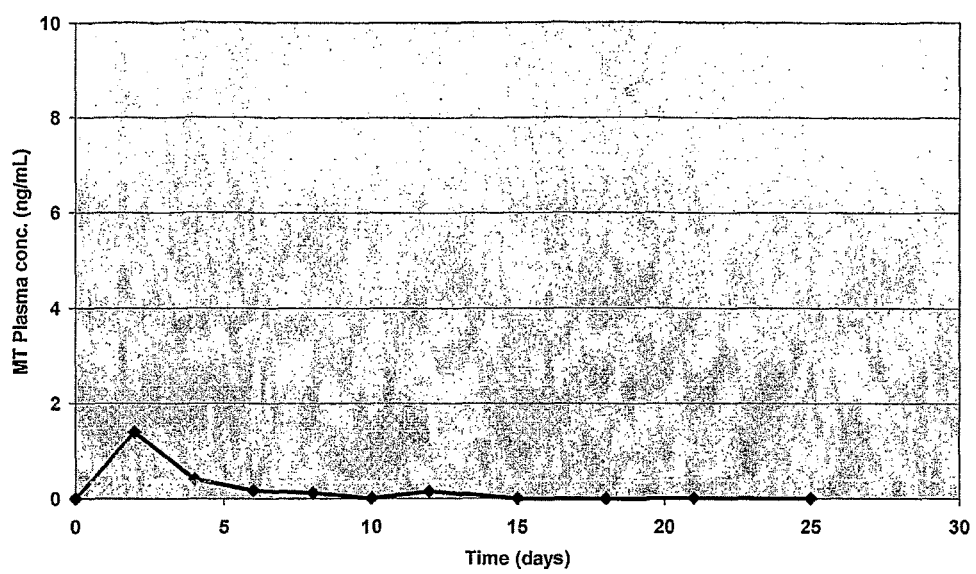
FIG. 5 shows the pharmacokinetic data from Study 3 described herein.
Figure 6:
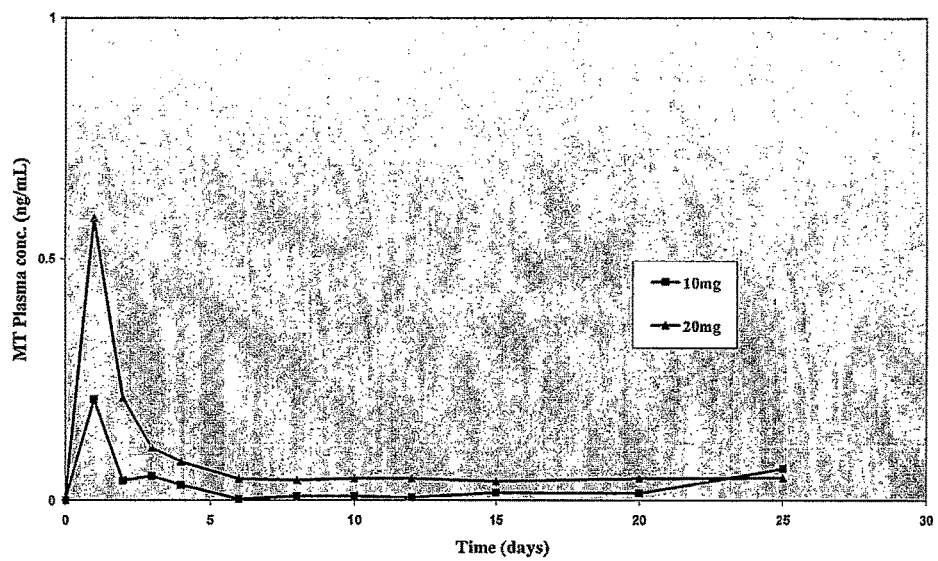
FIG. 6 shows the pharmacokinetic data from Study 4 described herein.

Based upon the data in Tables 2, 3 and 4, FIGS. 4, 5 and 6 reveal that the peak levels of Melanotan in the plasma of subjects that received a liquid injection was approximately 100 times greater than levels of Melanotan in the plasma of the subjects that had received the controlled release dose of Melanotan.

The following Tables 5, 6, 7 and 8 list the responses of the subjects for each of the studies following the different dosing regimes of Melanotan in terms of the change in melanin density (MD) measured at the inner upper arm after 30, 90 and 60 days for Studies 1, 2, 3 and 4 respectively. The inner upper arm generally denotes a person's constitutive skin melanin since environmental exposure appears to be least in this area.

TABLE 5

Melanin Density Change from
Baseline (Inner Upper Arm) for Study 1

| Day 9 | Day 30 |
|---|---|
| 0.51 ± 0.55 | 0.48 ± 0.53 |

TABLE 6

Melanin Density Change from
Baseline (Inner Upper Arm) for Study 2

| Day 12 | Day 30 | Day 40 | Day 60 |
|---|---|---|---|
| 0.28 ± 0.45 | 0.39 ± 0.49 | 0.61 ± 0.58 | 0.61 ± 0.66 |

TABLE 7

Melanin Density Change from
Baseline (Inner Upper Arm) for Study 3

| Day 10 | Day 21 | Day 30 | Day 60 |
|---|---|---|---|
| 1.31 ± 0.86 | 1.54 ± 0.72 | 1.84 ± 0.74 | 2.18 ± 0.64 |

TABLE 8

Melanin Density Change from
Baseline (Inner Upper Arm) for Study 4

|  | Day 4 | Day 10 | Day 21 | Day 30 | Day 60 |
|---|---|---|---|---|---|
| 10 mg | 0.417 | 0.465 | 0.638 | 0.677 | 1.345 |
| 20 mg | 0.300 | 0.791 | 0.946 | 1.384 | 2.114 |

Figure 7:
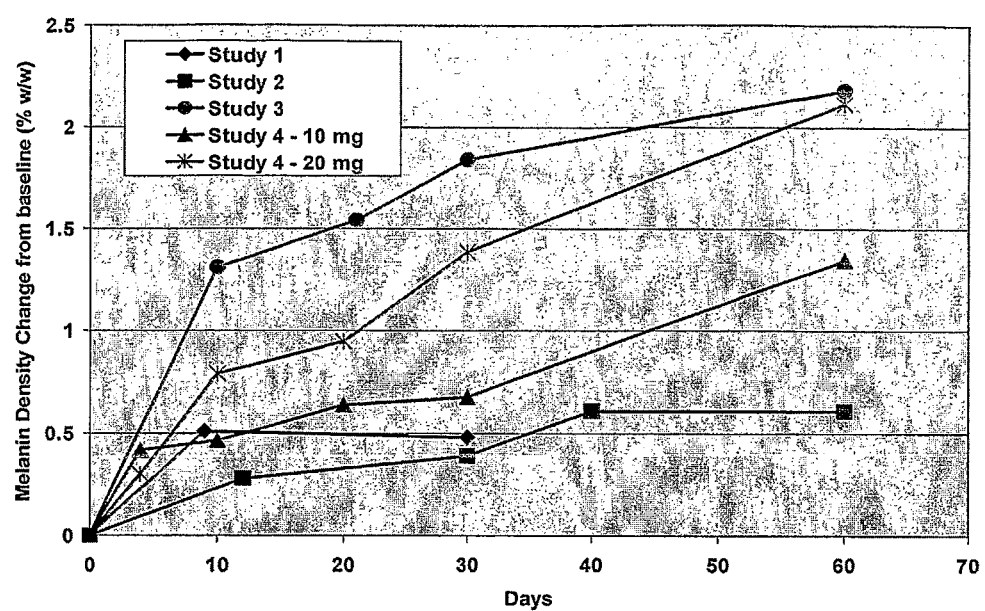
FIG. 7 shows the comparison of melanin density change (MD %) in the subjects in Studies 1, 2, 3 and 4 described herein.

Based on the data in Tables 5-8, FIG. 7 shows that the melanin density change of the subjects in Studies 3 and 4 was dramatically higher and quicker than for Studies 1 and 2. This unexpected result is to be viewed with the fact that the subjects in both Studies 3 and 4 received no more than a 1/15 of the dose of Melanotan overall, when compared with subjects in Study 2.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

REFERENCES

1. Hadley M E. The melanotropic hormones. In: Brake D, Editor. *Endocrinology*. 4th Edition, Simon & Schuster; (1982), p. 153-76.
2. Thody A J, et al. Pheomelanin as well as eumelanin are present in human epidermis. *J. Invest. Dermatol.* (1991), 97:340-44.
3. Valverde P, et al. Variants of the melanocyte-stimulating hormone receptor gene are associated with red hair and fair skin in humans. *Nature Genet.* (1995), 11:328-30.
4. Box N F. et al. Melanocortin-1 receptor genotype is a risk factor for basal and squamous cell carcinoma. *J Invest. Derm.* (2001), 116:224-29.
5. Palmer J S. et al. Melanocortin-1 receptor polymorphisms and risk of melanoma: is the association explained solely by pigmentation phenotype? *Am. J Hum. Genet.* (2000), 66:176-86.
6. Levine N, et al. Induction of skin tanning by subcutaneous administration of a potent synthetic melanotropin. *JAMA* (1991), 266:2730-736.
7. Sawyer T K, et al. [Nle$^4$-D-Phe$^7$)-α-melanocyte stimulating hormones: a highly potent α-melanotropin with ultralong biological activity. *Proc. Natl. Acad. Sci.* USA (1980), 77:5754-8.
8. Dorr R T, et al. Increased eumelanin expression and tanning is induced by a superpotent melanotropin [Nle$^4$-D-Phe$^7$]-α-MSH in humans. *Photochem. Photobiol.* (2000), 72:526-32.
9. Lipton J M, et al. Antiinflammatory effects of the neuropeptide alpha-MSH in acute, chronic and systemic inflammation. *Ann. NY. Acad. Sci.* (1994), 741:137-48.
10. Ceriani G, et al. The neuropeptide alpha-melanocyte-stimulating hormone inhibits experimental arthritis in rats. *Neuroimmunomodulation* (1994), 1:28-32.
11. Chiao H S, et al. α-melanocyte-stimulating hormone reduces endotoxin-induced liver inflammation. *J. Clin. Invest.* (1996), 97:2038-44.
12. Levine N, et al. Effects of a potent synthetic melanotropin, Nle$^4$-D-Phe$^7$-α-MSH (Melanotan-1) on tanning: a dose-ranging study. *J. Derm. Treat.* (1999), 19:127-32.
13. Bhardwaj, R, et al. In vitro characterisation and in vivo release profile of a poly(D,L-lactide-co-glycolide)-based implant delivery system for the α-MSH analog, Melanotan-1. *Int. J. Pharm.* (1998), 170:109-117.
14. Bhardwaj R, et al. Pharmacologic response of a controlled-release PLGA formulation for the alpha-melanocyte stimulating hormone analog, Melanotan-1. *Pharmaceutical Research* (2000), 17:583-9.
15. Bhardwaj, R, et al. Controlled-release delivery system for the α-MSH analog, Melanotan-1 using Polyoxamer 407. *J. Pharm. Sci.* (1996), 15:915-919.
16. Fitzpatrick T B. The validity and practicality of sun-reactive skin types I through VI. *Arch. Dermatol.* (1988), 124: 869-871.
17. Graham J H. Precancerous lesions of the skin. *Primary Care* (1975), 2: 699-766.
18. Stenback F. Life history and histopathology of ultraviolet light-induced skin tumours. *National Cancer Institute Monograph* (1978), 50: 57-70.
19. De L. Castrucci A M et al. Synthesis and studies of superpotent melanotropins resistant to enzyme degradation. *Comp. Biochem. Physiol.* (1984), 78B: 519-524.
20. Hadley M E et al. [Nle$^4$-D-Phe$^7$]-α-MSH: a superpotent melanotropin that "irreversibly" activates melanoma tyrosinase. *Endocr. Res.* (1985), 11:157-170.
21. Dawson B V et al. Administration of melanotropic peptides during gestation in the rodent. *Toxicol.* (1993), 77: 91-101.
22. Dorr R T et al. Toxicologic studies of a superpotent melanotropin, [Nle$^4$-D-Phe$^7$]-α-MSH. *Invest. New Drugs* (1988), 6: 251-258.
23. Darr R T. and Dawson B V. Toxicology report: Results of a 30 day study of MELANOTAN-I given subcutaneously to adult rats. *University of Arizona internal report.* (1988).
24. Dorr R T. Thirty day Toxicology study of Melanotan-I [Nle$^4$-D-Phe$^7$]-α-MSH in miniature Yucatan swine. *University of Arizona, Laboratory Booklet—Chris Brooks* (1993).
25. Levine N et al. Effects of a potent synthetic melanotropin, Nle$^4$-D-Phe$^7$-α-MSH (Melanotan-1) on tanning: Dose ranging study. *J. Dermatol. Treat.* (1999), 10 (2): 127-132.
26. Dorr R T et al. Increased eumelanin expression and tanning is induced by a superpotent melanotropin [Nle$^4$-D-Phe$^7$]-α-MSH in humans. *Photochem & Photobiol.* (2000).

27. Evans A et al. A Randomised, Placebo-Controlled, Double-Blind Study to Assess the Pharmacokinetics and Tanning Effect of Melanotan in Healthy Adult Subjects *Study Report August* (2000).
28. Dwyer T et al. The use of spectrophotometry to estimate melanin density in Caucasians. *Cancer Epidemiology, Biomarkers & Prevention* (1998), 7: 203-206.
29. Sanchez, et al. Role of G protein coupled receptor kinases in the homologous desensitization of the human and mouse melanocortin 1 receptors. *Pigment Cell Res* (2003), 16 (5): 593-4.

The invention claimed is:

1. A method for inducing melanogenesis in a human subject comprising administering to the subject an alpha-MSH analogue in an effective amount and time to induce melanogenesis by melanocytes in epidermal tissue of the subject, wherein the alpha-MSH analogue is [Nle$^4$, D-Phe$^7$]-alpha-MSH, wherein the alpha-MSH analogue is administered in a delivery system that releases the alpha-MSH analogue in the subject for at least 2 days, and wherein the alpha-MSH analogue is administered at a level not exceeding 10 ng/ml in plasma of the subject for a period of at least 24 hours.

2. A method for reducing occurrence of UV radiation-induced skin damage in a human subject comprising administering to the subject an alpha-MSH analogue in an effective amount and time to induce melanogenesis by melanocytes in epidermal tissue of the subject, wherein the alpha-MSH analogue is [Nle$^4$, D-Phe$^7$]-alpha-MSH, wherein the alpha-MSH analogue is administered in a delivery system that releases the alpha-MSH analogue in the subject for at least 2 days, and wherein the alpha-MSH analogue is administered at a level not exceeding 10 ng/ml in plasma of the subject for a period of at least 24 hours.

3. The method of claim 1, wherein the delivery system comprises up to 20 mg of alpha-MSH analogue.

4. The method of claim 1, wherein the delivery system comprises from 5 mg of alpha-MSH analogue.

5. The method of claim 1, wherein the delivery system comprises from 10 mg to 20 mg of alpha-MSH analogue.

6. The method of claim 1, wherein the alpha-MSH analogue is released for at least 4 days.

7. The method of claim 1, wherein the alpha-MSH analogue is released for at least 6 days.

8. The method of claim 1, wherein the level is not exceeding 2 ng/ml in the plasma of the subject.

9. The method of claim 1, wherein the period is at least 2 days.

10. The method of claim 1, wherein the period is at least 4 days.

11. The method of claim 1, wherein the delivery system comprises from 5 to 60% of alpha-MSH analogue.

12. The method of claim 1, wherein the delivery system is administered subcutaneously.

13. The method of claim 1, wherein the delivery system is a rod or implant.

14. The method of claim 2, wherein the delivery system comprises up to 20 mg of alpha-MSH analogue.

15. The method of claim 2, wherein the delivery system comprises from 5 mg of alpha-MSH analogue.

16. The method of claim 2, wherein the delivery system comprises from 10 mg to 20 mg of alpha-MSH analogue.

17. The method of claim 2, wherein the alpha-MSH analogue is released for at least 4 days.

18. The method of claim 2, wherein the level is not exceeding 2 ng/ml in the plasma of the subject.

19. The method of claim 2, wherein the period is at least 4 days.

20. The method of claim 2, wherein the delivery system is administered subcutaneously.

21. The method of claim 1, wherein the delivery system comprises an extended release formulation.

22. The method of claim 2, wherein the delivery system comprises an extended release formulation.

* * * * *